United States Patent [19]
Mombrinie

[11] Patent Number: 5,380,278
[45] Date of Patent: Jan. 10, 1995

[54] LIQUID CLEANSING AND EVACUATION METHOD AND APPARATUS FOR USE IN SURGICAL PROCEDURES

[76] Inventor: Pierre Mombrinie, 3208 Bruce Dr., Fremont, Calif. 94539

[21] Appl. No.: 904,762

[22] Filed: Jun. 26, 1992

[51] Int. Cl.$^6$ ............................................. A61M 1/00
[52] U.S. Cl. ........................................ 604/35; 604/28; 15/228
[58] Field of Search ................ 604/35, 36, 290, 367, 604/371, 131–133, 73, 48, 54, 27, 28, 51, 313, 315, 118, 119, 46, 49, 289, 310; 433/91–94; 602/44, 45, 47, 49, 52, 56; 15/228, 229.1–229.5, 98, 245, 49.1

[56] References Cited

U.S. PATENT DOCUMENTS

| | | | |
|---|---|---|---|
| 2,777,148 | 1/1957 | Belsky et al. | 15/228 |
| 4,351,081 | 9/1982 | Tarkinson | 15/98 X |
| 4,421,505 | 12/1983 | Schwartz | 604/28 |
| 5,171,391 | 12/1992 | Chmielewski et al. | 156/229 |
| 5,175,050 | 12/1992 | Meirowitz et al. | 428/290 |
| 5,215,539 | 6/1993 | Schoolman | 604/280 |
| 5,230,626 | 7/1993 | Larson et al. | 433/136 |

*Primary Examiner*—C. Fred Rosenbaum
*Assistant Examiner*—V. Alexander

[57] ABSTRACT

A method for cleansing operative tissue during a surgical procedure includes providing a cleansing liquid for application to the operative tissue in a region of surgical activity where the surgical procedure is being performed, continuously bathing the operative tissue in the region of surgical activity with the liquid and continuously evacuating the liquid from the region of surgical activity by drawing a vacuum through a perforate member covered with hydrophilic wicking material and having liquid spreading material interposed between the perforate member and the hydrophilic wicking material thereby to distribute the liquid to be evacuated as wicked by the wicking material over the surface of the perforate member. Apparatus for evacuating liquid from a region of surgical activity where a surgical procedure is being performed responsible to a drawn vacuum of preselected magnitude includes a perforate tubular ring, a fitting communicating with the interior of the ring and adapted for vacuum communicating connection to a source of the drawn vacuum, a liquid permeable textile covering in the form of a sleeve fitting around the exterior of the tubular ring and preferably nylon retaining rings for retaining the textile sleeve-like covering in fixed position around and respecting the ring.

33 Claims, 1 Drawing Sheet

U.S. Patent    Jan. 10, 1995    5,380,278
FIG. 1
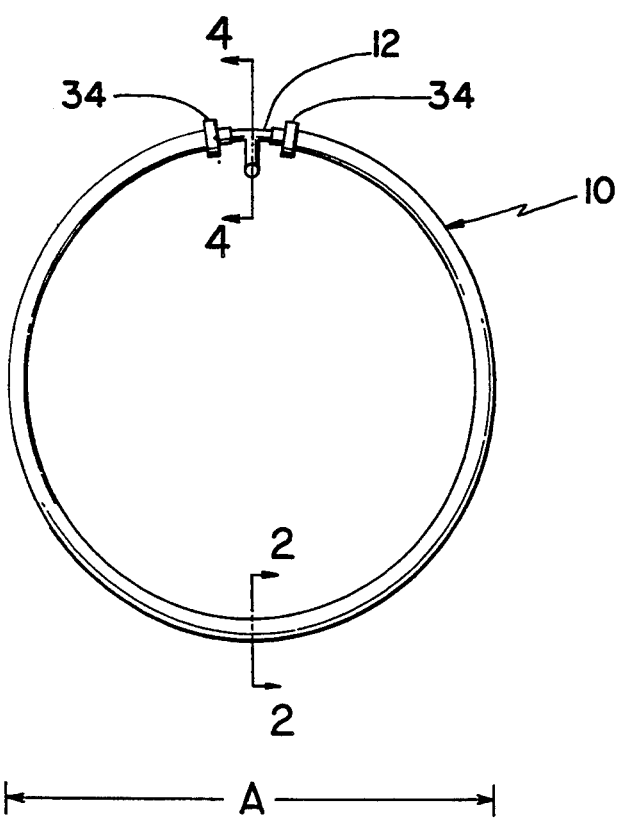
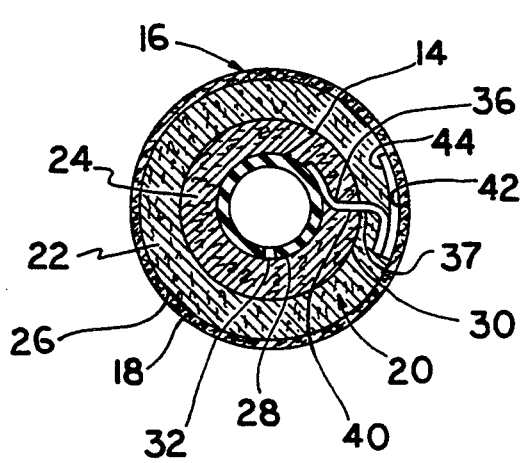
FIG. 2
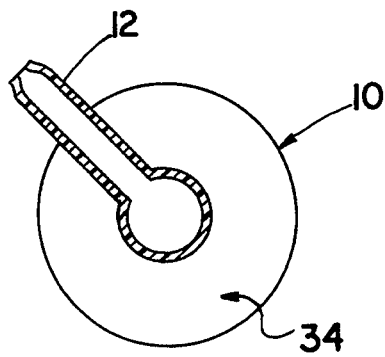
FIG. 4
FIG. 3
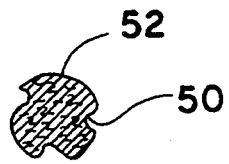

LIQUID CLEANSING AND EVACUATION METHOD AND APPARATUS FOR USE IN SURGICAL PROCEDURES

FIELD OF THE INVENTION

This invention is in the field of surgery and relates to methods and apparatus used to evacuate cleansing and/or sanitizing liquid from a region in which a surgical procedure is performed.

BACKGROUND OF THE INVENTION

It is common practice in many surgical procedures to bathe the region of surgical activity, where the surgical procedure is being performed, with liquid. The liquid may be water or some other liquid. The liquid may be provided to cleanse the region by removing debris, such as small pieces of tissue cut away by a surgeon during a surgical procedure, from the region.

The liquid may also be provided to sanitize the region, where there is danger of infection during the surgical procedure.

The liquid may further be provided to cool the region, such as in dental procedures where cooling liquid is directed towards the point at which the dentist's drill contacts the teeth. The cooling liquid reduces the temperature of the teeth during drilling, thereby reducing the discomfort associated with such dental procedures.

During arthroscopic surgery as typically performed on the knee, the liquid may be confined within the knee by the patient's skin. However, there is inevitably some leakage of liquid at the incision through which the liquid is supplied to the knee interior; the need exists to evacuate that liquid from the area outside the knee which is proximate to the region of surgical activity.

Heretofore, such cleansing and antiseptic liquids have typically been permitted to collect on the floor of an operating room when such liquids are used in general surgical procedures. A disadvantage attendant to the conventional practice of permitting the cleansing or other liquid to collect on the operating room floor is that the liquid sometimes creates hazardous footing conditions, contributing to slipping and sliding by operating room personnel during the operating procedure with resultant danger to the patient.

For dental procedures, suction devices are placed into the mouth to remove cooling water. These suction evacuators are reasonably effective but have an attendant disadvantage of producing significant noise as the cooling water is evacuated from the patient's mouth.

SUMMARY OF THE INVENTION

In one of its aspects, this invention provides a method for cleansing operative tissue during a surgical procedure. The method includes providing liquid for application to the operative tissue in a region of surgical activity where the procedure is being performed. Operative tissue in the region is preferably continuously bathed with the liquid.

The liquid is continuously evacuated from the region of surgical activity by drawing a vacuum through a perforate member. The perforate member is preferably covered with liquidphilic, preferably hydrophilic, wicking material, to distribute the liquid to be evacuated, as the liquid is wicked by the wicking material, over the surface of the perforate member.

Most desirably, the perforate member is in the form of a perforate tubular ring, having a liquid permeable and hydrophilic textile covering fitting around the ring in the form of a sleeve. The ring is most desirably positioned inboard of the periphery of the region of surgical activity so that the surgical procedure is performed substantially within the ring. Vacuum is drawn through the ring during the surgical procedure so that the liquid is evacuated from the region of surgical activity. The vacuum is preferably of magnitude sufficient to draw the liquid gently through and along the sleeve-like covering of the perforate ring and thereafter through the perforations into the ring interior.

In another of its aspects, this invention provides apparatus for evacuating liquid from a region of surgical activity where a surgical procedure is being performed, where the liquid evacuation is performed responsively to a drawn vacuum of preselected magnitude. The apparatus desirably includes a perforate tubular ring and a fitting communicating with the interior of the ring, where the fitting is adapted for vacuum communicating connection to the drawn vacuum.

In yet another of its aspects, this invention provides apparatus for evacuating liquid from the floor of an operating room or other theater in which surgical activity is performed.

A liquid permeable textile covering desirably fits around the exterior of the tubular ring and desirably includes a knit sleeve and hydrophilic wicking material between the ring and the sleeve. Most desirably, the fibers of the sleeve are grooved for increased wicking action.

The wicking material is desirably substantially comprised of synthetic fibers and is most preferably polyester, so that the wicking material provides a transfer path for the liquid, rather than absorbing the liquid. Most desirably, the wicking material is a two layer lamina with the surface of the lamina facing the ring being melt-blown and the outwardly facing surface being spun bound.

The apparatus further desirably includes means for retaining the textile covering in relatively fixed position around and respecting the ring. The means for retaining the textile covering in fixed position around and respecting the ring desirably further includes annular ring-like means which fit circumferentially about the perforate tubular ring on respective sides of a fitting connected to the ring and through which the vacuum is drawn, squeezing the textile covering against the perforate tubular ring. Most desirably, these annular ring-like squeezing means are nylon or some other non-metallic material.

The means for retaining the textile covering in fixed position around and respecting the perforate tubular ring desirably further comprises adhesive means contacting the perforate tubular ring and presenting an adhesive surface to at least a portion of the surface of the wicking material which contacts the perforate tubular ring.

In its most desirable configuration, the perforate tubular ring is about three-eighths inch inner diameter and includes perforations defined by holes of about 0.020 inches in diameter. Desirably, the perforations are spaced about two millimeters apart along the circumferential direction of the perforate tubular ring and are axially aligned.

DESCRIPTION OF THE DRAWINGS

FIG. 1 is a top view of apparatus for evacuating liquid from a region of surgical activity embodying aspects of the invention.

FIG. 2 is a sectional view taken at lines and arrows 2—2 in FIG. 1.

FIG. 3 is a sectional view of yarn used in fabricating the knit sleeve portion of the apparatus illustrated in FIGS. 1 and 2.

FIG. 4 is a sectional view taken at lines and arrows 4—4 in FIG. 1.

DESCRIPTION OF THE PREFERRED EMBODIMENTS AND BEST MODE KNOWN FOR PRACTICING THE INVENTION

Referring to the drawings in general and to FIG. 1 in particular, a preferred embodiment of apparatus for evacuating liquid from a region of surgical activity where a surgical procedure is being performed is designated generally 10 and is of closed, ring-like configuration. Apparatus 10 extends around a 360 degree circle and includes a fitting 12 connected to respective ends of a perforate tubular ring 14 defining the central portion of apparatus 10. Perforate tubular ring 14 is illustrated in section in FIG. 2. Fitting 12 is adapted for vacuum communicating connection between the hollow interior of perforate tubular ring 14 and a source of drawn vacuum of preselected magnitude.

Apparatus 10 further includes a liquid permeable textile covering designated generally 16 in FIG. 2 where covering 16 is preferably in sleeve-like form. Covering 16 preferably includes a preferably knit outer sleeve 18 and liquidphilic, preferably hydrophilic, wicking material 20 positioned between ring 14 and sleeve 18.

The wicking material designated generally 20 in FIG. 2 is preferably a two layer lamina with the outer layer designated generally 22 and the inner layer designated generally 24. The outwardly facing surface 26 of outer layer 22 of the wicking material lamina is preferably spun bound. The inner surface 28 of inner layer 24 of the two layer wicking material lamina is preferably meltblown. The interface between the inner and outer layers of the two layer wicking material lamina 22, 24 is designated 30 in FIG. 2.

Tubular ring 14 includes perforations 32, one of which is illustrated in FIG. 2. Perforations 32 are preferably holes of about 0.020 inch diameter, made by drilling through the wall of tubular ring 14 with a number 76 drill. Most preferably, perforations 32 are about two millimeters apart and are evenly circumferentially spaced around ring 14. Further preferably, perforations 32 are axially parallel, with all perforations 32 communicating with the exterior surface of ring 14 at a common angular position respecting the axis of ring 14.

As best illustrated in FIG. 4, fitting 12 is angularly disposed out of and respecting the plane defined by ring 14, which is the plane of the paper in FIG. 1. This angular disposition of fitting 12 assures that when the apparatus for evacuating liquid is placed on a wet floor, perforations 32 in ring 14 face the floor. This maximizes the liquid sucking action of apparatus 10 and contributes to efficient evacuation of liquid from a floor or other surgical activity region.

Experimentation has shown that perforations 32 may be as small as 0.015 inch diameter and as large as about 0.090 inch diameter. Perforation diameter of 0.020 inches seems to be optimal; there is some drop-off in the liquid pick-up performance as perforation diameter decreases or increases from the 0.020 inches optimum. When the perforation diameter size is less than 0.015 inches, liquid, particularly water, will not be drawn by the apparatus at any reasonable level of vacuum drawn within the interior of ring 14. When perforation diameter exceeds 0.060 inches, drop-off in performance becomes significant; when perforation diameter exceeds about 0.090 inches, the perforations are too large to provide any significant suction effect at any reasonable level of vacuum.

Perforate tubular ring 14 is preferably about 11 inches in overall diameter as indicated by dimension "A" in FIG. 1. Wicking material 20 preferably is about 0.2 inches in overall thickness, as indicated by dimension "B" in FIG. 2, with lamina 22 and 24 having substantially equal thickness.

Liquid permeable textile covering 16 is retained in place on perforate tubular ring 14 in part by annular means, designated generally 34 in FIG. 1, fitting circumferentially about perforate tubular ring 14 on either side of fitting 12 for squeezing liquid permeable textile covering 16 against perforate tubular ring 14. These circumferential squeezing means 34 are preferably nonmetallic and are most preferably nylon. Suitable squeezing means are available as Part No. P-4-18-0 from Plas-Ties, Inc. in Santa Ana, Calif.

Fitting 12 is desirably a black nylon "T" connector sold as a connector having catalog number T0-6WP by Eldon James of Loveland, Colo.

The means for retaining liquid permeable textile covering 16 in position about ring 14 further includes adhesive means contacting ring 14 and presenting an adhesive surface to an axially elongated edge or extremity 35 of wicking material 20; this adhesive means includes first adhesive means designated generally 36 in FIG. 2.

First adhesive means 36 is preferably conventional masking tape, having adhesive on a single side thereof. In FIG. 2, adhesive means 36 has adhesive on the side thereof designated 40 in FIG. 2.

The adhesive means portion of the retaining means further includes second adhesive means 42 which is similarly preferably conventional single-backed masking tape having an adhesive side 44 which facingly contacts both the non-adhesive side 46 of first adhesive means 36 and a longitudinally extending outwardly facing surface edge portion of outer layer 22 of the wicking material lamina.

Adhesive contacts between adhesive side 44 of means 42 and non-adhesive side 46 of adhesive means 36 effectively secures wicking material lamina 20 about perforate tubular ring 14. Knit outer sleeve 18 provides extra support and protection for wicking material 20.

Knit outer sleeve 18 is preferably knitted from dacron polyester fiber, available from DuPont Fibers in Wilmington, Del. The dacron polyester fiber from which outer sleeve 18 is knit is preferably grooved, as illustrated in FIG. 3, with grooves 50 being provided about the periphery 52 of each yarn of the fiber. Grooves 50 extend generally axially respecting the fiber and impart improved wicking capability to the dacron polyester fiber. Preferably, outer sleeve 18 is knit in a single knit fashion using a single size 20 yarn. Dixie Yarns spins the polyester fiber into yarn; Zens Industrial Knits knits the yarn into the tubular knit defining outer sleeve 18.

Wicking material 20 is preferably microporous and is preferably of the type known in the trade as "universal sorbent" and is believed to include both polypropylene and cellulose, with some surfactant added to enhance the wicking capability of the material. Suitable wicking material is available from Matarah Industries, Inc. in Milwaukee, Wis.

Most desirably, wicking material 20 is a two layer lamina with the exterior surface of wicking material 20 being spun bound to provide a somewhat slick outwardly facing surface for easy sliding of knit outer sleeve 18 thereover, while the surface of wicking material 20 facingly contacting tubular ring 14 is preferably melt-blown to provide a fluffy, high liquid transmissivity surface contacting perforate tubular ring 14.

First and second adhesive means are preferably both three-quarter inch wide masking tape available from Santa Rosa Paper Company in Santa Rosa, Calif. Tubular ring 14 is preferably three-eighths inch inner diameter by 0.455 inches outer diameter black polypropylene hose available from Mission Irrigation Supply Company in Fremont, Calif.

During operation, the vacuum desirably drawn to effectuate efficient water and other liquid sucking by perforate tubular ring 14 is in the order of 200 millimeters of water. Vacuums as low as 50 millimeters of water can be used, but below about 100 millimeters of water efficiency drops substantially.

During operation wicking material 20 tends to become soaked with liquid, whereupon substantially only water (and/or other liquid) enters tubular ring 14 in response to the vacuum. Very little air enters tubular ring 14 once wicking material 20 is soaked with water or other liquid. As a result, the invention exhibits high water removal capabilities.

The desirable ring-like configuration of the apparatus in the preferred embodiment permits the apparatus to lie flat on the floor. The inclined orientation of fitting 12 together with the planar configuration of perforate tubular ring 14 ensures that apparatus 10 lies flat on a floor with perforations 18 facing the floor. This enhances operation.

During operation when a vacuum is drawn, apparatus 10 does not stick to the floor; suction through perforations 32 does not cause the apparatus to suck down to the floor. Similarly, during operation a large amount of water does not cause apparatus 10 to float away. Apparatus 10 can be stepped on without it breaking and does not have to be submerged or even entirely within a water puddle in order to evacuate substantially all of the water puddle from the floor. When only half of apparatus 10 contacts a water puddle, the apparatus nevertheless picks up substantially about 90% of the water puddle, which the apparatus would pick up entirely if the apparatus were in full contact with the puddle and suction is initiated.

The small light-weight character of the apparatus facilitates disposal after use, which is important for sanitary reasons in a hospital operating room environment. The light weight of the apparatus and compact size in the preferred embodiment makes the apparatus easy to ship. Additionally, the apparatus is largely made of recyclable materials, thereby alleviating any environmental concerns.

While the principal use of the apparatus is that of evacuating water, urine, blood and other liquids from operating room floors, the apparatus may also be used in the course of practicing a method for cleansing operative tissue during surgery. When operative tissue is bathed with a liquid during a surgical procedure, the apparatus illustrated in FIG. 1 may be positioned so that the surgery is substantially performed within the perforate tubular ring while vacuum is drawn through the perforate tubular ring. In such case, if the operative tissue is continuously bathed with liquid, apparatus 10 continuously removes that liquid from the surgical region by vacuum drawn through the perforate tubular ring 14. In this regard, the preferred vacuum of about 200 millimeters of water has been found quite sufficient to successfully gently draw liquid through and along sleeve 18, through perforations 32 and into the interior of perforate tubular ring 14.

When the apparatus has been constructed in the preferred configuration and dimensions and operated according to the parameters noted above, it has been found to be exceedingly quiet, nearly silent, during operation. This is an important feature since it is important to eliminate extraneous noise in hospital operating rooms.

While the apparatus has been depicted in a ring-like configuration, this is not required. The apparatus may be configured as needed for a particular application.

While the preferred embodiment of the invention has been described above and alternative embodiments have also been described, the scope of protection to which the invention is believed entitled is defined by the claims and by equivalents thereto which perform substantially the same function in substantially the same way to achieve substantially the same result as set forth in the claims, so long as such substantial equivalents, as defined by a claim for such substantial equivalent, do not read on the prior art.

I claim:

1. A method for cleansing operative tissue during surgery, comprising:
   a. continuously bathing said operative tissue in a region of surgical activity with liquid; and
   b. continuously evacuating said liquid from said surgical activity region by drawing a vacuum through a perforate member covered with liquidphilic wicking material extending about said region of surgical activity.

2. The method of claim 1 wherein said evacuating further comprises positioning a perforate tubular ring having an endless internal passage, having a liquid permeable and liquidphilic textile covering fitting around the ring exterior, so that said surgery is substantially performed within said ring and thereafter drawing said vacuum through said ring.

3. A method for cleansing operative tissue during surgery, comprising:
   a. positioning a tubular ring having an endless internal passage, having perforations spaced along said ring, said perforations being substantially about 0.060 inches or less in diameter, having a liquid permeable and liquidphilic substantially synthetic textile sleeve-like cover fitting circumferentially around the ring exterior and substantially along the length of the axis of the ring, inboard of the periphery of said region of surgical activity so that said surgery is substantially performed within said ring;
   b. providing a cleansing liquid for application to said operative tissue in a region where said surgery is performed;
   c. continuously bathing said operative tissue in said surgical region with said liquid; and
   d. continuously evacuating said liquid from said surgical region by drawing a vacuum through said ring of magnitude sufficient to gently draw said liquid through and along said sleeve-like cover, through said perforations and into said ring interior.

4. A method for removing liquid from a floor, comprising:
   a. positioning a tubular ring having an endless internal passage, having perforations spaced therealong and having a liquid permeable and hydrophilic substantially synthetic textile sleeve fitting circumferentially around the ring exterior and substantially along the length of the axis of the ring, on said floor and contacting said liquid on said floor with said perforations facing said floor;
   b. evacuating said liquid from said floor by drawing a vacuum through said ring of magnitude sufficient to gently draw liquid on said floor and contacting said ring through and along said sleeve, through said perforations and into said ring interior.

5. Apparatus for evacuating liquid from a region of surgical activity where a surgical procedure is being performed, responsively to a drawn vacuum of preselected magnitude, comprising:
   a. a perforate tubular ring having an endless internal passage;
   b. a fitting communicating with the interior of said ring for vacuum communicatingly connecting said ring interior to said drawn vacuum;
   c. a liquid permeable textile covering around the exterior of said tubular ring, comprising:
      i. a sleeve; and
      ii. liquidphilic wicking material between said ring and said sleeve; and
   d. means for retaining said textile covering in fixed position around and respecting said ring.

6. Apparatus of claim 5 wherein said wicking material is a two layer lamina, the surface thereof facing said ring being melt blown and the outwardly facing surface being spun bound.

7. Apparatus of claim 5 wherein said fitting is axially elongated and extends from said ring in a direction skew to a plane defined by said ring.

8. Apparatus of claim 7 wherein said fitting extends in a direction substantially opposite from said perforations in said ring.

9. Apparatus of claim 5 wherein said sleeve is knit and fibers of said sleeve are axially grooved for enhanced wicking action.

10. Apparatus of claim 5 wherein said wicking material comprises cellulose.

11. Apparatus of claim 10 wherein said wicking material comprises polyester.

12. Apparatus of claim 5 wherein said wicking material comprises polyester.

13. Apparatus of claim 5 wherein said means for retaining said textile covering in fixed position around and respecting said ring further comprises:
   a. means fitting circumferentially about said ring proximate said fitting, for squeezing said covering against said ring.

14. Apparatus of claim 13 wherein said circumferential squeezing means is non-metallic.

15. Apparatus of claim 14 wherein said circumferential squeezing means is nylon.

16. Apparatus of claim 13 wherein said means for retaining said textile covering in fixed position around and respecting said ring further comprises adhesive means contacting said ring and presenting an adhesive surface to said textile covering facing said ring.

17. Apparatus of claim 16 wherein said adhesive means comprises a web axially elongated in the direction of tube elongation.

18. Apparatus of claim 17 wherein a first side of said web contacts said tube and an axially extending first edge of the wicking material, separating the contacted edge from a second axially extending edge of the wicking material contacting a second side of the web.

19. Apparatus of claim 18 wherein said adhesive means comprises a second web axially elongated in the direction of tube elongation, one side thereof contacting said first adhesive web along and a remaining side thereof contacting said sleeve.

20. Apparatus of claim 13 wherein said means for retaining said textile covering in fixed position around and respecting said ring further comprises adhesive means contacting said ring and presenting an adhesive surface to a surface of said textile covering facing said ring.

21. Apparatus of claim 20 wherein said adhesive means comprises a web.

22. Apparatus of claim 5 wherein said ring is about $\frac{3}{8}$ inch inner diameter.

23. Apparatus of claim 5 wherein diameter of said perforations is at most about 10% of tube inner diameter.

24. Apparatus of claim 5 wherein adjacent perforations are spaced apart at least about 2 times perforation diameter.

25. Apparatus of claim 5 wherein said ring perforations are defined by holes of about 0.020 inch diameter.

26. Apparatus of claim 25 wherein perforations of said ring are less than about $\frac{1}{4}$ inch apart.

27. Apparatus of claim 5 wherein said perforations are circumferentially aligned.

28. Apparatus of claim 27 wherein said perforations are axially parallel.

29. Apparatus of claim 28 wherein said perforations face in a common axial direction.

30. Apparatus for evacuating liquid from a region of surgical activity responsively to a drawn vacuum, comprising:
   a. a perforate elongated member vacuum communicatingly connected to said drawn vacuum;
   b. hydrophilic material overlying said perforate region of said elongated member of thickness about ten times diameter of said perforations in said elongated member; and
   c. means for retaining said hydrophilic material in fixed position overlying said perforate region of said elongated member.

31. Apparatus for evacuating liquid from a region of surgical activity where a surgical procedure is being performed, responsively to a drawn vacuum of preselected magnitude, comprising:
   a. a perforate tubular member of about $\frac{3}{8}$ inch inner diameter, said member perforations being defined by holes of about 0.020 inch diameter spaced less than about $\frac{1}{4}$ inch apart along the axial length of said member;
   b. a fitting connectedly communicating with the interior of said member, for vacuum communicatingly connecting said tubular member interior with said drawn vacuum;
   c. a liquid permeable textile covering fitting around said tubular member including a knit sleeve and liquidphilic substantially synthetic polyester wicking material between said member and said sleeve; and d. means for retaining said textile covering in fixed position around and respecting said member including non-metallic axially elongated means fitting circumferentially about said member proximate said fitting for squeezing said covering against said member and adhesive means wrapped around said member and presenting an adhesive surface to a surface of said textile covering facing said member.

32. Apparatus of claim 31 wherein said member is a ring.

33. A substantially silent method for removing liquid from a region of surgical activity, comprising:

a. positioning a hydrophilic material over and along perforations of an elongated tubular member with said hydrophilic material being of thickness of about ten times diameter of said perforations in said tubular member in the region of contact with said perforate portion of said tubular member;

b. positioning said hydrophilic material to contact said liquid to be removed while positioning said tubular member so that said portion of said hydrophilic material overlying said perforations is substantially proximate to said liquid to be removed;

c. drawing a vacuum in said elongated member of about 200 millimeters of water to gently draw liquid contacting said hydrophilic member through and along hydrophilic member, through said perforations and into said member interior.

* * * * *